United States Patent [19]

Harreld

[11] Patent Number: 5,460,618
[45] Date of Patent: Oct. 24, 1995

[54] SIDE SLIT CATHETER

[75] Inventor: John H. Harreld, San Luis Osbispo, Calif.

[73] Assignee: MiniMed Inc., Sylmar, Calif.

[21] Appl. No.: 262,784

[22] Filed: Jun. 20, 1994

[51] Int. Cl.⁶ ............................................. A61M 5/00
[52] U.S. Cl. ..................... 604/264; 604/27; 604/257; 604/280
[58] Field of Search ................................ 604/280, 264, 604/257, 258, 275, 247, 161, 43, 27

[56] References Cited

U.S. PATENT DOCUMENTS

| | | |
|---|---|---|
| 4,373,527 | 2/1983 | Fischell . |
| 4,385,635 | 5/1983 | Ruiz ........................................... 604/280 |
| 4,573,994 | 3/1986 | Fischell et al. . |
| 4,723,947 | 2/1988 | Konopka . |
| 4,801,297 | 1/1989 | Mueller . |
| 4,976,703 | 12/1990 | Franetzki et al. . |

Primary Examiner—John D. Yasko
Attorney, Agent, or Firm—Kelly Bauersfeld & Lowry

[57] ABSTRACT

An improved side slit catheter is provided for use in long term delivery of a selected medication to a patient, wherein the catheter has a distal end tip shaped to permit expulsion of an occlusive deposit. The catheter includes an elongated lumen for passage of medication such as insulin to the distal end tip for administration to the patient at a selected infusion site. The tip includes a cylindrical wall segment defining a tapered bore which expands in cross section to a delivery port, with at least one and preferably a plurality of longitudinal side slits formed in said wall segment. In the event of delivery port occlusion, medication delivery at normal pressure will continue through the side slits. The occlusion can be expelled from the catheter tip by delivering a selected fluid through the catheter at elevated pressure, whereupon the slitted catheter tip deformably responds to detach from and thus permit expulsion of the occlusion.

9 Claims, 2 Drawing Sheets

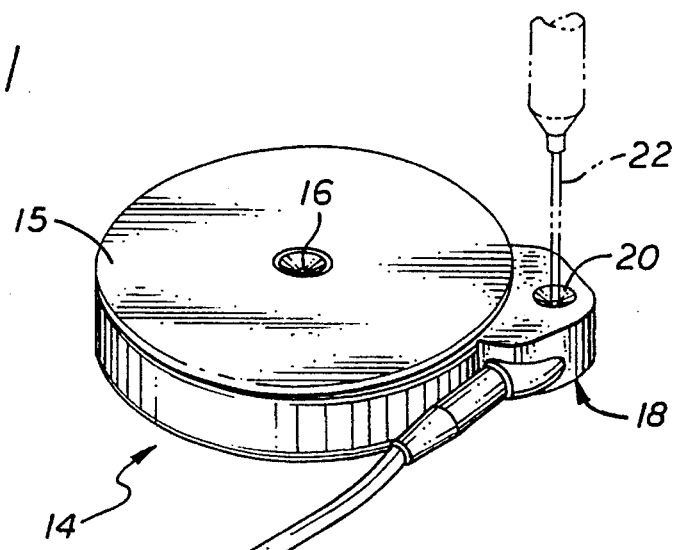
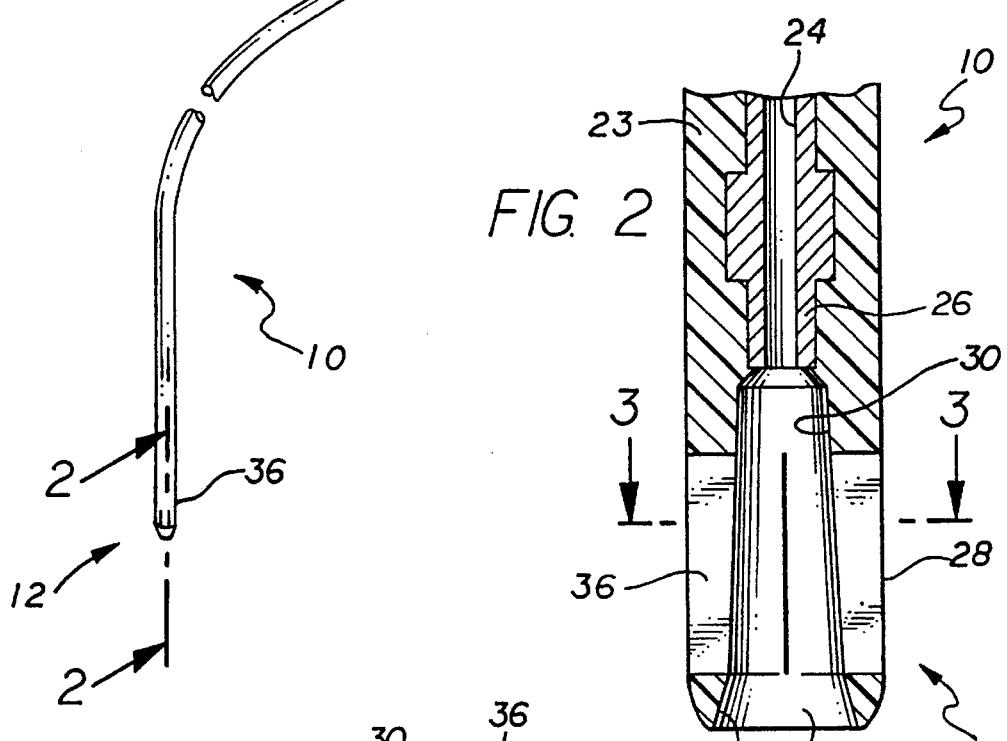
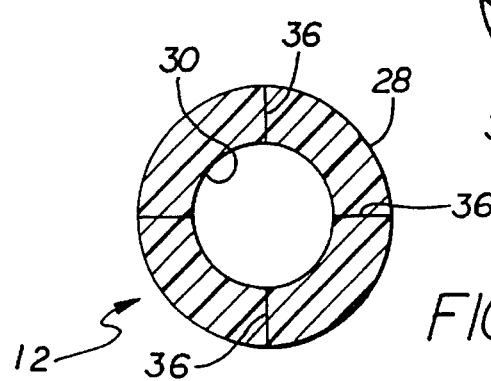

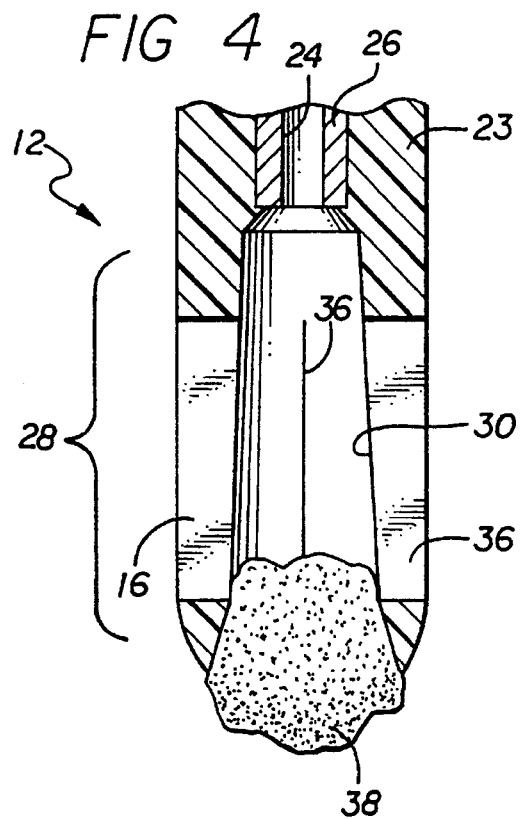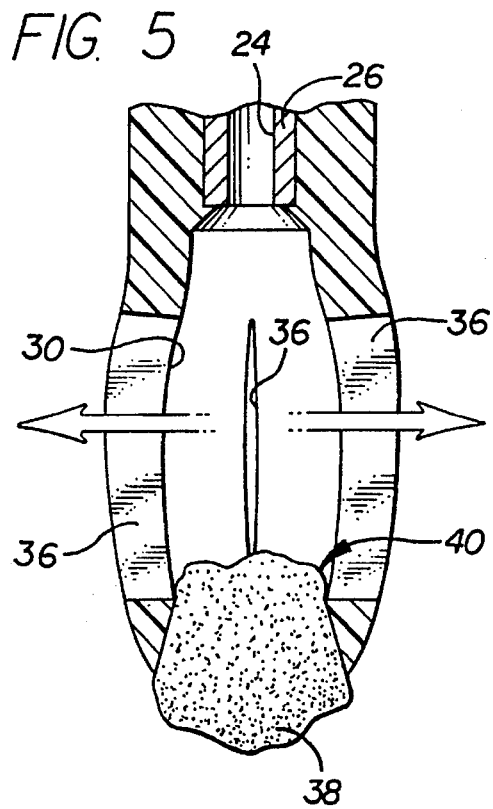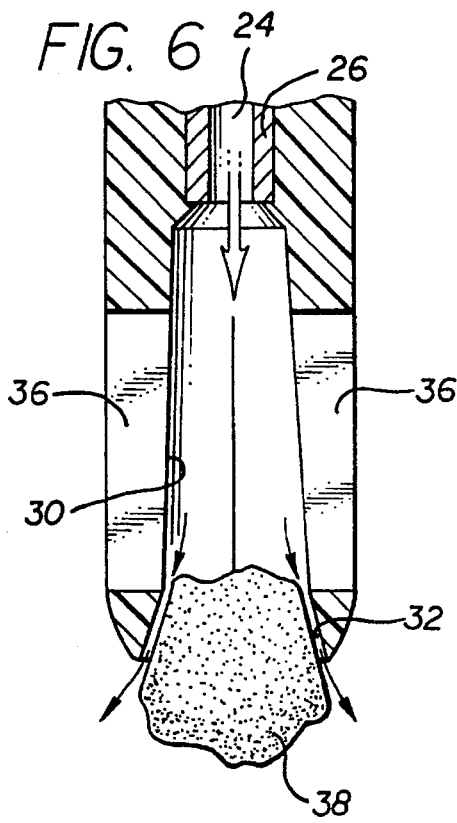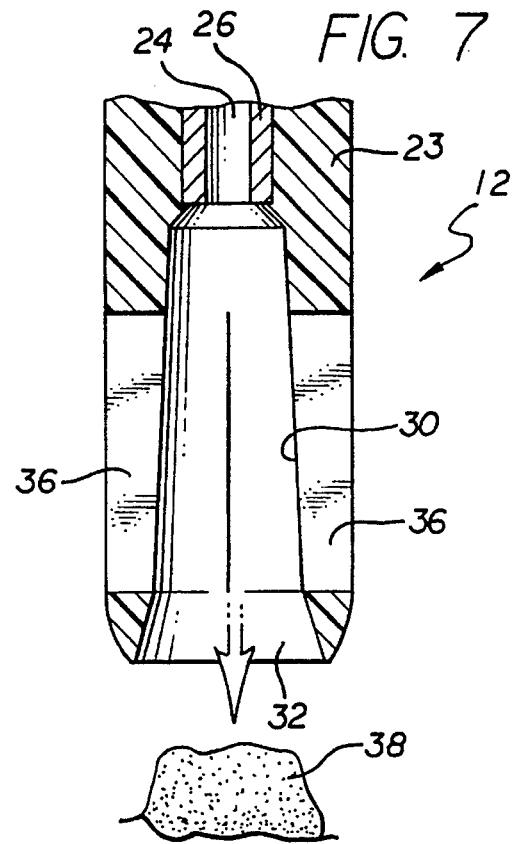

SIDE SLIT CATHETER

BACKGROUND OF THE INVENTION

This invention relates generally to improvements in catheters of the type used to administer a selected medication to a patient over an extended period of time. More specifically, this invention relates to a medication infusion catheter having an improved distal end tip which permits, on an as-needed basis, expulsion of an occlusive deposit.

Catheters are well-known in the medical arts for use in delivering medical fluids to or drawing body fluids from a patient. In one typical form, the catheter comprises an elongated tubular element adapted for transcutaneous placement, normally with the assistance of a withdrawable stylet needle. The catheter defines a narrow lumen or passage permitting transcutaneous fluid transfer to or from the patient. In another typical application, the catheter is implanted into the patient in association with an implantable infusion pump or similar instrument for programmed delivery of a selected medication such as insulin over an extended period of time. One such implantable infusion pump including an implantable catheter is shown, by way of example, in U.S. Pat. Nos. 4,373,527 and 4,573,994. In either case, the catheter is commonly constructed from a biocompatible polymer material, such as a medical grade silicone rubber.

In many patient treatment applications, it is necessary or desirable for the catheter to remain in place over an extended period of time which may range from several days to several years. One such long term application includes use in combination with an implantable medication infusion pump, as described above. In long term indwelling applications, however, the distal end tip of the catheter is susceptible to occlusions which appear to occur as a result of complex interactions involving the catheter material, and/or the simultaneous presence of infusion and body fluids. The likelihood of occlusion development appears to be increased when complex medications such as insulin are delivered to the patient. When an occlusion occurs, normal medication delivery to the patient is obstructed or prevented. Catheters have not been designed to provide an effective or practical way to achieve in situ occlusion removal. Surgical removal and replacement of a clogged catheter is not a desirable alternative.

There exists, therefore, a significant need for improvements in long term indwelling catheters, particularly with respect to providing a catheter tip which will facilitate and permit expulsion of an occlusive deposit. The present invention fulfills this need and provides further related advantages.

SUMMARY OF THE INVENTION

In accordance with the invention, an improved catheter is provided for use in long term delivery of a selected medication to a patient. The catheter is particularly designed for use, by way of example, in combination with a medication infusion pump for programmed delivery of a selected medication such as insulin to a patient over an extended period of time. The improved catheter includes a distal end tip shaped to permit expulsion of an occlusive deposit, without requiring surgical access to or removal of the catheter from the patient.

In accordance with the preferred form of the invention, the distal end tip includes a generally cylindrical wall segment formed from a resilient material such as medical grade silicone rubber and defining a tapered bore which leads with a progressively expanding cross section to an open delivery port. The wall segment defining said tapered bore includes at least one and preferably a plurality of longitudinally extending side slits which terminate at a point spaced slightly upstream from the delivery port. In use, in the event that the delivery port becomes obstructed by deposits and/or accumulations of fibrin-based tissue or the like, the side slits permit medication outflow under normal pressures for uninterrupted delivery of the medication to the patient. In addition, in response to delivery of a selected fluid through the catheter at an elevated pressure, the slitted tip deformably responds to detach or delaminate from the occlusion and thereby permit pressure-caused expulsion of the occlusion.

Other features and advantages of the present invention will become more apparent from the following detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 1 is a fragmented perspective view illustrating an improved side slit catheter embodying the novel features of the invention, and shown for use in combination with an implantable medication infusion pump;

FIG. 2 is an enlarged fragmented vertical sectional view taken generally on the line 2—2 of FIG. 1;

FIG. 3 is an enlarged fragmented horizontal sectional view taken generally on the line 3—3 of FIG. 2;

FIG. 4 is an enlarged fragmented sectional view similar to FIG. 2 and illustrating an occlusion obstructing a catheter delivery port; and FIGS. 5–7 are fragmented sectional views similar to FIG. 4, and illustrating pressure responsive deformation of the catheter tip to expel the occlusion.

DETAILED DESCRIPTION OF THE PREFERRED EMBODIMENT

As shown in the exemplary drawings, an improved catheter referred to generally by the reference numeral 10 is provided for delivering a selected medication or the like to a patient. The catheter 10 includes a distal end tip 12 having a specific geometry to permit expulsion of occlusive deposits which can form over an extended period of time, and which could otherwise obstruct medication delivery to the patient.

The catheter 10 is shown in FIG. 1 in combination with an implantable medication infusion pump 14 of a type designed for direct implantation into the body of a patient. In this regard, the infusion pump 14 comprises an hermetically sealed case or housing 15 formed from a biocompatible material, typically such as titanium or titanium alloy. A primary inlet or refill port 16 is provided on the pump housing to receive a hypodermic needle (not shown) to permit transcutaneous refilling of a medication storage reservoir therein. During normal operation, a pump mechanism within the pump housing 15 is programmably operated by an appropriate control circuit to deliver the medication via the catheter 10 in accordance with individual patient requirements. The distal end tip 12 of the catheter 10 is normally placed at a selected medication infusion site, such as the intraperitoneal space in the case of insulin administration to a diabetic patient. For a more detailed description of the overall construction and operation of implantable infusion pumps of this general type, including the construction of the refill port 16, see U.S. Pat. Nos. 4,373,527 and 4,573,994, which are incorporated by reference herein.

The illustrative infusion pump 14 additionally includes a side port assembly 18 mounted at one side of the implantable pump housing. As shown, the side port assembly 18 includes a secondary so-called side access port 20 adapted to receive a hypodermic needle 22 in order to permit transcutaneous access to a medication flow path at a point between the discharge side of the pump mechanism, and the upstream end of the catheter 10. In this regard, the catheter 10 is suitably mounted to the side port assembly 18, and extends therefrom to the distal end tip 12 through which the medication is delivered to the patient. For a more detailed description of the construction and operation of the side port assembly 18, including a preferred catheter mounting thereto, see U.S. Ser. No. 08/221,569, filed Apr. 1, 1994, entitled IMPLANTABLE MEDICATION INFUSION PUMP WITH DISCHARGE SIDE PORT, which is incorporated by reference herein.

As shown in FIGS. 1–3, the catheter 10 comprises an elongated and relatively flexible length of tubing 23 (FIG. 2) formed from a biocompatible material, such as a surgical grade silicone or silicone-based elastomer. The catheter defines an elongated lumen 24 for flow passage of the selected medication from the pump 14 to the distal end tip 12. As shown in a preferred arrangement, the lumen 24 extends through an inner liner 26 of polyethylene or the like, particularly when the catheter is used to administer insulin to a diabetic patient, wherein the liner 26 is formed as by comolding within the outer tubing 23. In this regard, the polyethylene liner 26 exhibits a high degree of compatibility with insulin as described, for example, in U.S. Pat. No. 4,723,947.

The distal end tip 12 of the catheter 10 comprises a short cylindrical wall segment 28 defining a tapered bore 30 which extends from the downstream end of the liner 26 to an open medication delivery port 32. More specifically, the upstream end of the tapered bore 30 has a relatively small diametric size, corresponding substantially to the diametric size of the lumen 24. The tapered bore segment 30 extends from the liner 26, generally coaxially with the lumen 24, and with a progressively increasing diametric cross sectional size toward the delivery port 32. At the delivery port, as shown in FIG. 2, the tapered bore 30 blends with a relatively sharp bevel 34. In one preferred configuration, the tapered bore extends for an axial length of about 0.2 inch, with a bore size ranging from about 0.03–0.05 inch at the upstream end to about 0.07–0.09 inch at the downstream end.

At least one and preferably a plurality of longitudinal side slits 36 are formed in the wall segment 28 at the catheter distal end tip. These side slits 36, four of which are depicted in FIGS. 2 and 3, are shown at equiangular intervals about the circumference of the wall segment 28, and extend from an upstream position located near the upstream end of the tapered bore 30, to a downstream end disposed in slight spaced relation to the distal plane of the catheter tip. Accordingly, at the delivery port 32, the catheter tip defines an uninterrupted annular ring of resilient material having, for example, an axial length on the order of about 0.03–0.05 inch. Thus, the side slits 36 are closed-ended, and the natural resiliency of the catheter tip material causes the side slits 36 to be normally retained in a substantially closed and non-deformed geometry, as viewed in FIG. 3.

The catheter 10, as described, functions in a normal manner to administer medication from the pump 14 to the patient, at the selected medication infusion site. During normal operation, the medication flows through the catheter lumen 24 and further through the open delivery port 32 for administration to the patient. In a typical application in combination with the implantable infusion pump 14, normal medication delivery pressures are on the order of 5 psi.

Over a period of time, occlusive deposits can form at the catheter delivery port 32, resulting in substantial obstruction of that flow path and thereby preventing desired administration of medication to the patient. Such occlusive deposits are believed to be the result of complex chemical interactions at the delivery port involving the catheter material, and/or the simultaneous presence of specific medication and body fluids. An occlusion 38 is shown in FIG. 4, obstructing the delivery port 32 and protruding upstream a short distance within the tapered bore 30.

In accordance with one aspect of the invention, the axial lengths of the tapered bore 30 and side slits 36 are chosen to extend upstream beyond the typical and anticipated location of an occlusion 38. With this geometry, normal medication delivery, for example, from the infusion pump 14, is not prevented by the presence of the occlusion 38. Rather, the medication pumped under normal pressures is free to flow outwardly from the catheter tip 12, by pressure flow passage through the side slits 36. Such normal medication delivery flow is illustrated in FIG. 5.

In addition, the improved catheter 10 of the present invention is designed to accommodate relatively quick and easy occlusion expulsion, thereby reopening the delivery port 32 to resumed medication flow, without requiring direct surgical access to the catheter tip. More specifically, a hypodermic needle 22 as shown in FIG. 1 may be used to access the side port assembly 18, for purposes of delivering a selected fluid such as saline solution or other suitable rinse/flush solution to the catheter 10, with controlled elevated pressure relative to normal pump delivery pressure. The delivery of such pressurized fluid to the catheter 10 causes the slitted catheter tip to expand and bulge outwardly, as viewed in FIG. 5, with the fluid passing through the side slits 36. This outward deformation of the wall segment 28 is accompanied by progressive delamination of the wall segment from the occlusion 38, as referenced by arrow 40. As this delamination occurs, the force retaining the occlusion 38 becomes smaller. Thus, with partial delamination of the tip 12 from the occlusion 38, the fluid pressure eventually expels the occlusion 38 from the delivery port 32, as viewed in FIGS. 6 and 7. In one working embodiment of the invention, the pressurized fluid was delivered via the side port assembly 18 at a pressure up to about 200 psi. After expulsion of the occlusion, normal pump operation may be resumed with normal and unobstructed medication delivery through the open delivery port 32 to the patient. This occlusion expulsion procedure can be performed as often as needed, without significant inconvenience to or discomfort by the patient.

The improved catheter 10 of the present invention thus provides a simple yet effective catheter tip geometry to permit occlusive deposits to be expelled when required. Pump performance for medication delivery can thus be maintained for an extended period of time.

A variety of modifications and improvements to the invention described herein will be apparent to those skilled in the art. Accordingly, no limitation on the invention is intended by way of the foregoing description and accompanying drawings, except as set forth in the appended

What is claimed is:

1. In a catheter for use in delivering a selected medical fluid to a patient, the improvement comprising a distal end tip having a generally cylindrical wall segment defining a tapered bore which expands in cross sectional size to a delivery port, said wall segment having at least one longitudinally extending side slit formed therein and having a downstream end terminating in spaced relation to said delivery port whereby said wall defines an uninterrupted annular ring adjacent said delivery port, said wall segment deformably responding upon occlusion of said delivery port to permit fluid delivered through said catheter to said tip to flow outwardly through said side slit;

said side slit and said tapered bore having upstream ends located at a position sufficiently upstream from said delivery port so that said upstream ends are spaced from any occlusion obstructing said delivery port whereby said distal end tip deformably responds to supply of a fluid to said catheter at a selected elevated pressure to cause said wall segment to detach from such occlusion and thereby permit pressure-caused expulsion of such occlusion from said delivery port.

2. The improved catheter of claim 1 wherein said at least one side slit comprises a plurality of longitudinally extending said slits formed in said wall segment and each having a downstream end terminating in spaced relation to said delivery port.

3. The improved catheter of claim 2 wherein said plurality of side slits are formed about the circumference of said wall segment generally in an equiangular spaced array.

4. The improved catheter of claim 1 wherein said catheter distal end tip is formed from a resilient medical grade elastomer.

5. A medication infusion system, comprising:

an infusion pump for pumping a selected medication to a patient; and a catheter defining a lumen for delivery of the selected medication from the pump to the patient, said catheter having distal end tip formed by a generally cylindrical wall segment defining a tapered bore which expands in cross sectional size to a delivery port, said wall segment having at least one longitudinally extending side slit formed therein and having a downstream end terminating in spaced relation to said delivery port whereby said wall defines an uninterrupted annular ring adjacent said delivery port, said wall segment deformably responding upon occlusion of said delivery port to permit fluid delivered through said catheter to said tip to flow outwardly through said side slit;

said side slit and said tapered bore have upstream ends located at a position sufficiently upstream from said delivery port so that said upstream ends are spaced from any occlusion obstructing said delivery port whereby said distal end tip deformably responds to supply of a fluid to said catheter at a selected elevated pressure to cause said wall segment to detach from such occlusion and thereby permit pressure-caused expulsion of such occlusion from said delivery port.

6. The system of claim 5 wherein said at least one side slit comprises a plurality of longitudinally extending said slits formed in said wall segment and each having a downstream end terminating in spaced relation to said delivery port.

7. The improved catheter of claim 6 wherein said plurality of side slits are formed about the circumference of said wall segment generally in an equiangular spaced array.

8. The improved catheter of claim 5 wherein said catheter distal end tip is formed from a resilient medical grade elastomer.

9. The system of claim 5 further including a side port assembly coupled between said pump and an upstream end of the catheter, said side port assembly including means for permitting injection of a selected fluid under elevated pressure to said catheter.

* * * * *